United States Patent
Müller et al.

(10) Patent No.: US 10,940,480 B2
(45) Date of Patent: Mar. 9, 2021

(54) FLOW CELL FOR A DISSOLUTION TEST DEVICE

(71) Applicant: ERWEKA GmbH, Heusenstamm (DE)

(72) Inventors: Werner G. Müller, Frankfurt am Main (DE); Levent Bozkurt, Rosbach (DE)

(73) Assignee: ERWEKA GmbH, Heusenstamm (DE)

( * ) Notice: Subject to any disclaimer, the term of this patent is extended or adjusted under 35 U.S.C. 154(b) by 41 days.

(21) Appl. No.: 15/895,486

(22) Filed: Feb. 13, 2018

(65) Prior Publication Data

US 2019/0046973 A1 Feb. 14, 2019

(30) Foreign Application Priority Data

Feb. 13, 2017 (DE) ..................... 10 2017 102 761.0

(51) Int. Cl.
| | |
|---|---|
| *B01L 3/00* | (2006.01) |
| *G01N 33/15* | (2006.01) |
| *G01N 21/05* | (2006.01) |
| *G01N 13/00* | (2006.01) |
| *G01N 1/38* | (2006.01) |
| *B01D 35/04* | (2006.01) |
| *G01N 35/00* | (2006.01) |

(52) U.S. Cl.
CPC ............. *B01L 3/508* (2013.01); *B01D 35/04* (2013.01); *G01N 1/38* (2013.01); *G01N 13/00* (2013.01); *G01N 21/05* (2013.01); *G01N 33/15* (2013.01); *B01D 2201/342* (2013.01); *B01L 2200/026* (2013.01); *B01L 2200/06* (2013.01); *B01L 2200/0689* (2013.01); *B01L 2200/087* (2013.01); *B01L 2200/14* (2013.01); *B01L 2300/0681* (2013.01); *B01L 2300/0832* (2013.01); *G01N 2013/006* (2013.01); *G01N 2035/00198* (2013.01)

(58) Field of Classification Search
CPC ........................................................ G01N 1/00
See application file for complete search history.

(56) References Cited

U.S. PATENT DOCUMENTS 3,240,342 A * 3/1966 Callahan, Jr. .......... B01D 35/02
210/232
4,181,853 A 1/1980 Abu-Shumays

FOREIGN PATENT DOCUMENTS

DE 31 33 373 A1 7/1982

* cited by examiner

*Primary Examiner* — Jyoti Nagpaul
(74) *Attorney, Agent, or Firm* — Troutman Pepper Hamilton Sanders LLP

(57) ABSTRACT

A flow cell for a dissolution test apparatus, Includes a cell mount, a filter head, a cylindrical cell casing connected with the cell mount and with the filter head via threads provided on respective ends of the cylindrical cell casing, and a sample cell received in the cell casing and co figured for receiving a sample.

10 Claims, 2 Drawing Sheets

FLOW CELL FOR A DISSOLUTION TEST DEVICE

CROSS-REFERENCES TO RELATED APPLICATIONS

This application claims the priority of German Patent Application, Serial No. 10 2017 102 761.0 filed Feb. 13, 2017, pursuant to 35 U.S.C. 119(a)-(d), the content of which is incorporated herein by reference in its entirety as if fully set forth herein.

BACKGROUND OF THE INVENTION

The present invention relates to a flow cell for a dissolution test apparatus and a corresponding dissolution test apparatus.

The following discussion of related art is provided to assist the reader in understanding the advantages of the invention, and is not to be construed as an admission that this related art is prior art to this invention.

Testing the properties of powdered and granular drugs, tablets, suppositories, implants and stents also includes testing their dissolution properties. For this purpose, the test specimens are placed in dissolution test equipment in a flow cell, where they are bathed with a test medium at a defined temperature and the amount of released active agent or dissolved specimen in the test medium is then recorded as a function of time.

In the state of the art, the term "flow cell" is often used exclusively for the cell, which in the present application is referred to as the "sample cell", and which receives the sample to be analyzed and through which the test medium flows. Sometimes this term is also used less precisely to refer to both the sample cell and to the entire cell with the cell casing and filter head surrounding the sample cell. In the context of this application, however, the term "flow cell" always means the entire structure of a measuring cell with the cell mount, the cell casing, the sample cell and the filter head.

The flow cells to be used are largely normalized or standardized in national and international pharmacopoeias in terms of their apparatus parameters and their mode of operation. Examples are the European Pharmacopoeia 5.0, chapter 2.9.3. "Dissolution test for solid dosage forms", pages 228 to 230, of 2005 and the United States Pharmacopeial Convention (USP) 2011, Chapter 711 "Dissolution", pages 1 to 8. The dissolution test devices consist of a water bath in which a heating coil for the test medium is located and on which the flow cell is mounted by means of the cell mount.

The test medium, which is usually an artificial gastric or intestinal fluid, is pumped at a constant flow rate through the heating coil into the sample cell where it dissolves the specimen. The test medium is tempered on the one hand in the heating coil to the test temperature and on the other hand simultaneously flushing of the cell casing with the water of the water bath ensures temperature control of the sample cell from the outside and thus temperature stability in the overall system.

The test medium flows through the sample cell via an inlet opening on the bottom of the cell in the direction of the outlet opening in the head of the cell. In between, the test medium flows through various elements that influence the flow (e.g. glass spheres), hold the respective samples or formulations and filter out residues. The type and number of elements and samples with which the sample cell is loaded depends on the test methods that are carried out. Accordingly, the respective matching cell heads are mounted. The topmost element of the sample cell before the outlet always forms a filter that retains undissolved particles in the cell. After leaving the sample cell through the outlet opening in the head, the test medium is then fed to a sample collector or an online measuring device (e.g. UV measuring device).

Since the flow cell and the sample cell have to be dismantled for cleaning and for loading with the test specimens, they are usually designed to be pluggable. During the test the individual parts are hereby held together by an electrical or mechanical clamping device, which presses the assembled parts from above onto the water bath or the cell mount fastened therein. The sealing is accomplished by toroidal O-ring seals, which are inserted either in grooves on the outer circumference of the parts and thus at the same time enable guiding and provisional mounting of the parts, or they are inserted between the head and filter. In the latter case, the underside of the head is then provided with a beveled edge region, so that the O-ring seal can be pressed outwards against the wall.

There are two different variants of the filters, depending on the type of sample cell used. The first variant, which is used predominantly for the measurement of granules, powders, stents and implants, is placed below the seal and consists of a supporting coarse mesh screen and a filter made of paper or glass fiber fleece placed thereon. These then contact the underside of the head, which for this purpose in its center has a cylinder which protrudes over the lower surface with which the head sits on the sealing ring, and which projects into the upper end of the sample space.

In the second variant, used predominantly for tablets and creams, the filter is placed above the seal and consists of a filter pack which is inserted into a recess in the lower end face of the head.

The document DE3133373A1 describes a device for examining particles with a first vessel for receiving an electrolytic liquid with particles suspended therein and an electrolyte-containing first chamber, an electrolyte-containing second chamber, a measuring aperture in the wall between the vessel and the first chamber, a scavenging port in the wall between the first chamber and the second chamber, an electrical current flow through the measuring aperture for generating detectable signals upon passage of particles through the measuring aperture, and a fluid circulation system which generates flow from the second chamber through a particulate-retaining filter into the first chamber, which is kept in motion by the kinetic energy of the suspension exiting through the measuring aperture. The flow cell described in this document has a housing body with two end parts, which are respectively screwed into the housing body at the opposite ends.

The document U.S. Pat. No. 4,181,853A describes a liquid chromatography apparatus in which a liquid fraction is conducted from a chromatography column through a flow cell filled with a stationary phase which absorbs the species to be absorbed, wherein the species to be measured is absorbed at the stationary phase in the flow cell and the measurement is accomplished by way of the emitted fluorescence excited in the species to be measured by irradiation of the species with electromagnetic radiation, and wherein the fluorescent species when measured in the equilibrium between the stationary and the mobile phase is measurable in the measuring cell by fluorescence in lower concentrations than in equilibrium only with the mobile phase. The flow cell can be connected to end caps in the liquid chromatography device which can be screwed to the flow cell.

However, in the state of the art sealing of the flow cells frequently involves problems that lead to leaks between the water circuit and the test medium circuit. As a result, water may enter and undesirably dilute the test medium or test medium may leak into the water where it causes impurities and loss of dissolved active ingredient or specimen.

Such measurement errors are already caused by minor inaccuracies in the alignment of the assembled parts. It is difficult to detect this error source during operation, unless a complete leakage of the cell occurs. As a result, the measurements are not reproducible and in the case of test protocols in which several samples are measured in parallel, large fluctuations occur within a set of measurements. In addition, leakage of test medium into the cell casing means a considerable loss of time for a series of measurements, since it is then not sufficient to merely re-load the sample cell for the next measurement, but the water in the water bath has to be exchanged and all flow cells and the water bath must be cleaned.

It would therefore be desirable and advantageous to achieve improved sealing of the flow cell while at the same time providing good cleanability and user-friendliness of the cells.

SUMMARY OF THE INVENTION

According to one aspect of the present invention a flow cell for a dissolution test apparatus includes a cell mount, a filter head, a cylindrical cell casing connected with the cell mount and with the filter head via threads provided on respective ends of the cylindrical cell casing, and a sample cell received in the cell casing and configured for receiving a sample.

An improved seal is thus achieved in that the conventional O-ring seals and an external clamping device for the inserted parts are dispensed with. Instead, the cylindrical cell casing is connected to the cell mount and the filter head respectively by means of a screw thread.

This enables secure guiding of the parts and at the same time allows for a user-friendly disassembly. Since no electrical or mechanical clamping device on the top of the cell head has to be attached during the screwing, the outlet opening for the test medium, which in the state of the art is always arranged on the side of the head, can be arranged on the top.

This also ensures improved flow guidance in the head area, because the 90° deflection of the flow is eliminated. A further result is a more uniform use of filter surfaces. According to the invention, the filter is arranged in the hollow, screwable filter head. The previously common variants can be omitted. The filter is housed uniformly as a filter pack in the filter head above the seal, allowing for easier insertion.

According to another advantageous feature of the present invention, the seal between the cell mount, with which the flow cell is mounted on the water bath, and the sample cell is accomplished via an end side flat gasket. Since the individual parts are accurately guided by the screwing and due to the fact that the flat gasket is configured wider than the torpid O-seals, a better seal is achieved, which is also less prone to handling errors of laboratory staff, since tilting can be practically ruled out.

According to another advantageous feature of the present invention, the sealing between the cell casing and the cell mount and between the cell casing and the filter head is accomplished with a respective end-face flat gasket. This reliably prevents leakage to the outside and within the filter head. Especially the latter area is critical for the measurements, due to the risk of mixing of water and test medium in this area.

According to another aspect of the present invention a dissolution test device includes at least one flow cell, wherein the at least one flow cell includes a cell mount, a filter head, a cylindrical cell casing connected with the cell mount and with the filter head via threads provided on respective ends of the cylindrical cell casing, and a sample cell received in the cell casing and configured for receiving a sample.

According to another advantageous feature of the present invention, the dissolution test apparatus includes seven flow cells according to the invention. This makes it possible to perform all test variants required for the dissolution tests in a single-pass run with a single apparatus.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
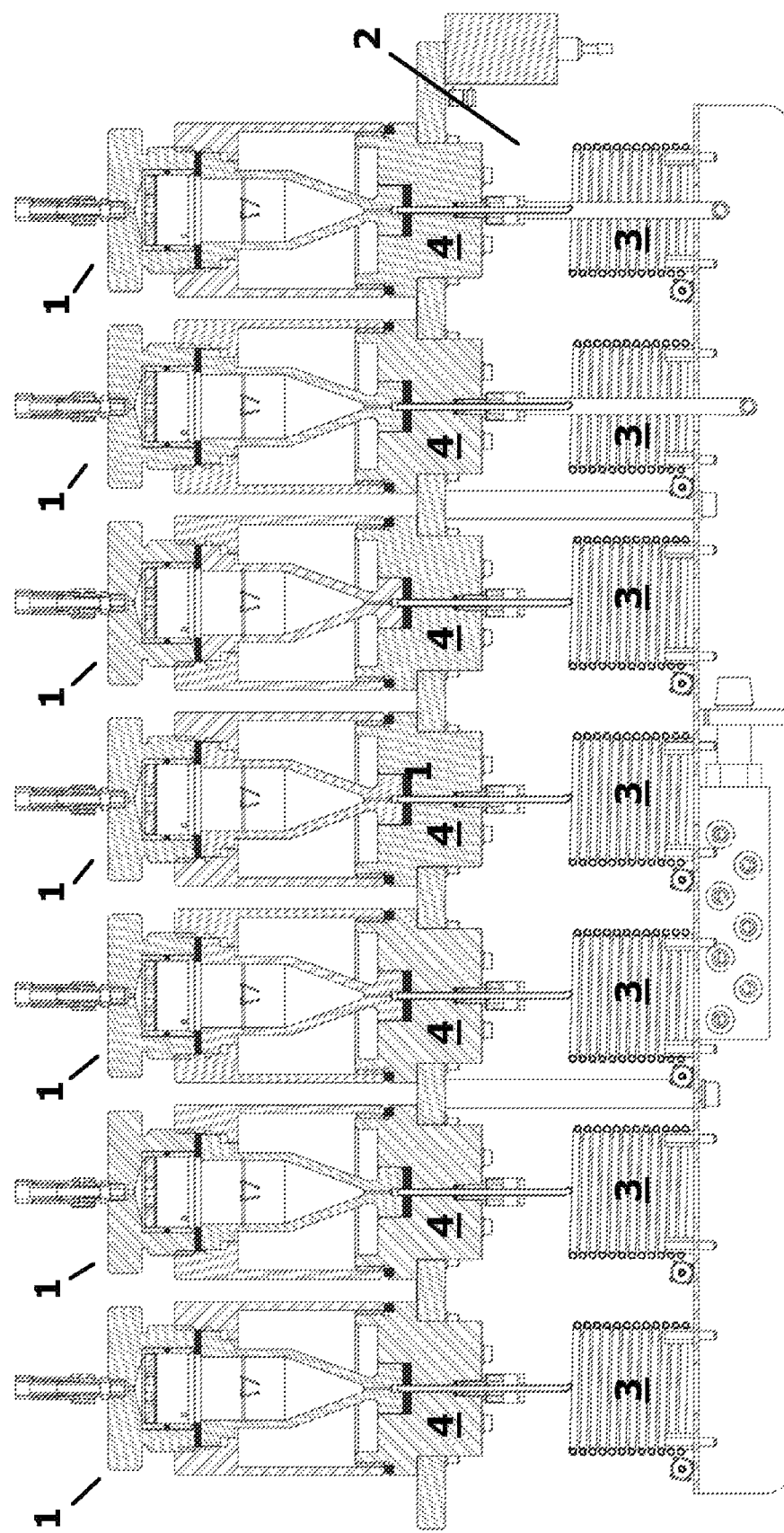
FIG. 1 shows a sectional view of an embodiment of a dissolution test device according to the invention.

Throughout all the Figures, same or corresponding elements may generally be indicated by same reference numerals. These depicted embodiments are to be understood as illustrative of the invention and not as limiting in any way. It should also be understood that the figures are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Turning now to the drawing, and in particular to FIG. 1, there is shown a sectional view of a preferred variant of the dissolution test device according to the invention with seven flow cells. By means of their cell mounts 4 the seven flow cells 1 are mounted on the water bath 2 of the test device into which the heating coils 3 of the flow cells 1 dip. The cell mounts 4 are firmly screwed to the upper part of the water bath 2, where they remain during normal operation of the device. For maintenance purposes, however, the cell mounts 4 can be removed after loosening the lateral screws.

Figure 2:
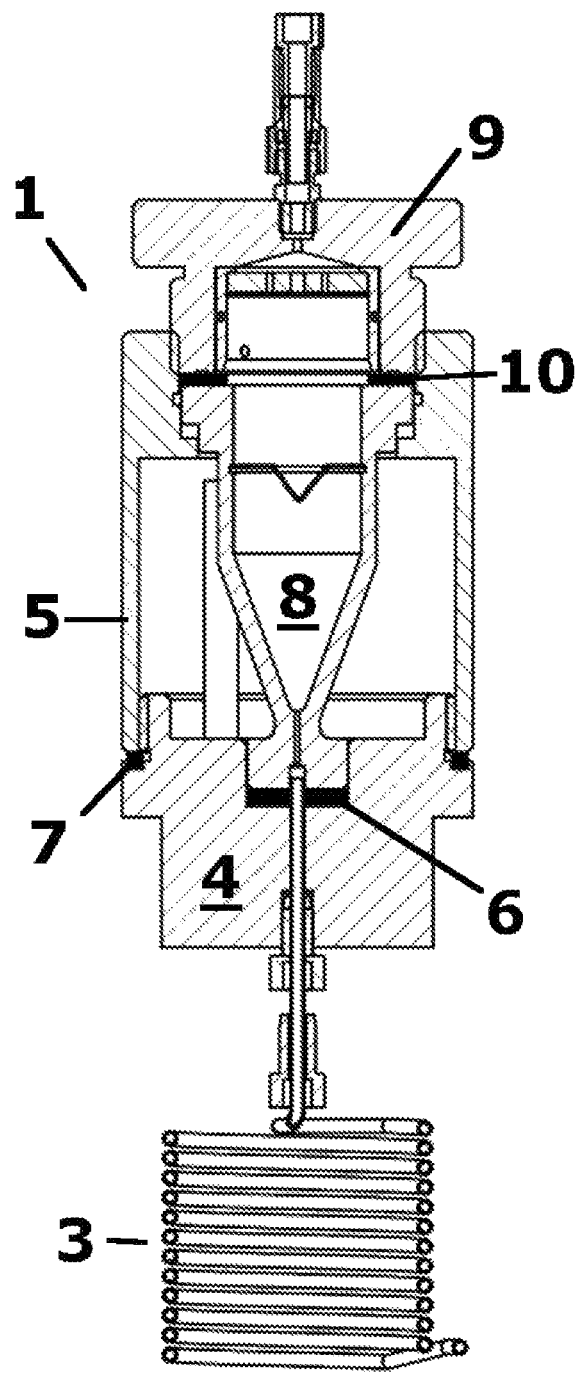
FIG. 2 shows a sectional view of a single flow cell according to the invention.

FIG. 2 shows a sectional view of a single flow cell 1 with its associated heating coil 3. The cell casing 5 has an internal thread with which it is screwed on the cell mount 4. In the center of the cell mount 4, a flat gasket 6 is inserted and in a groove on the outer circumference of the cell mount, the flat gasket 7 is inserted. The sample cell 8 is inserted In the center of the cell casing 5. Hereby, in the recess of the cell mount 4 the sample cell 8 sits with its bottom end face on the flat gasket 6, which has an opening for the test medium supply. The sealing of the cell casing 5 against the cell mount 4 is achieved by the front side flat gasket 7.

The screwable filter head 9, in which a filter pack is inserted, has an external thread with which it is screwed into the cell casing 5 from above. Hereby, the endside gasket 10 seals the filter head 9 against the cell casing 5 and the sample cell 8. The outlet for the test medium is arranged centrally on the top of the filter head 9.

To carry out the test, the sample is introduced into the sample cell 8. The space surrounding the sample cell 8 is flushed with water from the water bath for temperature control. The test medium is pumped at a constant flow rate through the heating coil 3 and is heated to the water bath temperature. Thereafter, the test medium flows through the inlet into the sample cell 8, flows around the sample and exits the sample cell 8 at the top through the filter pack and the outlet.

What is claimed as new and desired to be protected by Letters Patent is set forth in the appended claims and includes equivalents of the elements recited therein:

1. A flow cell for a dissolution test apparatus, comprising:
   a cell mount;
   a filter head;
   a cylindrical cell casing connected with the cell mount and with the filter head via threads provided on respective ends of the cylindrical cell casing;
   a water bath in which a heating coil for a test medium is located and on which the flow cell is mounted by means of the cell mount;
   a sample cell received in the cell casing and configured for receiving a sample, and
   an inlet opening on the bottom of the sample cell and an outlet opening in the head of the sample cell for pumping the test medium through the heating coil into the sample cell and through the filter pack and the outlet, wherein
   the sample cell sits with its bottom end face on a flat seal, which has an opening for the test medium supply, in a recess of the cell mount.

2. The flow cell of claim 1, further comprising a flat gasket arranged between the cell mount and the sample cell so as to seal the cell mount and the sample cell against each other.

3. The flow cell of claim 2, wherein the cell casing is sealed against the cell mount and against the filter head by respective further flat gaskets arranged between the cell casing and the cell mount and between the cell casing and the filter head.

4. The flow cell of claim 1, wherein the cell casing is sealed against the cell mount and against the filter head by respective flat gaskets arranged between the cell casing and the cell mount and between the cell casing and the filter head.

5. A method for carrying out a dissolution test with a dissolution test apparatus according to patent claim 1, comprising:
   introducing a sample into the flow cell;
   flushing the space surrounding the flow cell with water from the water bath for temperature control;
   pumping the test medium at a constant flow rate through the heating coil and heating it up to the water bath temperature; and
   flowing the test medium through the inlet into the flow cell, around the sample and exiting it the flow cell at the top through the filter pack and the outlet.

6. A dissolution test apparatus, comprising:
   at least one flow cell, said at least one flow cell comprising
      a cell mount;
      a filter head;
      a cylindrical cell casing connected with the cell mount and with the filter head via threads provided on respective ends of the cylindrical cell casing;
      a water bath in which a heating coil for a test medium is located and on which the flow cell is mounted by means of the cell mount,
      a sample cell received in the cell casing and configured for receiving a sample, and
      an inlet opening on the bottom of the sample cell and an outlet opening in the head of the sample cell for pumping the test medium through the heating coil into the sample cell and through the filter pack and the outlet, wherein
      the sample cell sits with its bottom end face on a flat seal, which has an opening for the test medium supply, in a recess of the cell mount.

7. The dissolution test apparatus of claim 6, further comprising a flat gasket arranged between the cell mount and the sample cell so as to seal the cell mount and the sample cell against each other.

8. The dissolution test apparatus of claim 7, wherein the cell casing is sealed against the cell mount and against the filter head by respective further flat gaskets arranged between the cell casing and the cell mount and between the cell casing and the filter head.

9. The dissolution test apparatus of claim 6, wherein the cell casing is sealed against the cell mount and against the filter head by respective flat gaskets arranged between the cell casing and the cell mount and between the cell casing and the filter head.

10. The dissolution test apparatus of claim 6, comprising seven said at least one flow cell.

\* \* \* \* \*